United States Patent [19]

Boden et al.

[11] Patent Number: 4,608,194

[45] Date of Patent: Aug. 26, 1986

[54] OXOBICYCLONONANE DERIVATIVES, PROCESS FOR PRODUCING SAME AND ORGANOLEPTIC USES THEREOF

[75] Inventors: Richard M. Boden, Ocean; John R. Helm, East Keansburg, both of N.J.

[73] Assignee: International Flavors & Fragrances Inc., New York, N.Y.

[21] Appl. No.: 763,569

[22] Filed: Aug. 8, 1985

[51] Int. Cl.[4] .................... A61K 7/46

[52] U.S. Cl. .................... 252/522 R; 252/174.11; 252/8.6; 560/256; 568/819; 558/265

[58] Field of Search .................... 560/256; 260/463; 568/819; 252/522 R, 174.11

[56] References Cited

U.S. PATENT DOCUMENTS

| | | | |
|---|---|---|---|
| 3,703,479 | 11/1972 | Theimer | 560/256 |
| 4,008,184 | 2/1977 | Mauaer et al. | 560/256 |
| 4,033,993 | 7/1977 | Bruns et al. | 260/463 |
| 4,080,309 | 3/1978 | Bruns et al. | 260/463 |
| 4,397,789 | 8/1983 | Boden et al. | 560/256 |
| 4,452,730 | 6/1984 | Boden et al. | 260/463 |
| 4,488,988 | 12/1984 | Licciardello et al. | 260/463 |

*Primary Examiner*—James H. Reamer
*Attorney, Agent, or Firm*—Arthur L. Liberman

[57] ABSTRACT

Described are oxobicyclononane derivatives having the generic structure:

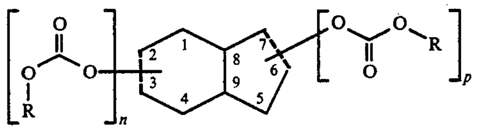

wherein R represents methyl or ethyl; wherein one of the dashed lines represents a carbon-carbon single bond or a carbon-carbon double bond; wherein N and P each represents 0 or 1 with the proviso that when N represents 1 the dashed line at the "2-3" position is a single bond with the sum of N and P being equal to 1 and uses thereof in augmenting or enhancing the aroma of perfume compositions, perfumed articles and colognes.

13 Claims, 14 Drawing Figures

GLC PROFILE FOR EXAMPLE I.
CRUDE

GLC PROFILE FOR EXAMPLE I,
BULKED FRACTIONS 4-7.

NMR SPECTRUM FOR PEAK "20" OF FIG. 2, EXAMPLE I.

IR SPECTRUM FOR PEAK "20" OF FIG.2, EXAMPLE I.

NMR SPECTRUM FOR PEAK "21" OF FIG. 2, EXAMPLE I.

IR SPECTRUM FOR PEAK "21" OF FIG. 2, EXAMPLE I.

NMR SPECTRUM FOR PEAK "12" OF FIG. 1, EXAMPLE I.

IR SPECTRUM FOR PEAK "12 OF FIG.1, EXAMPLE I

FIG.9
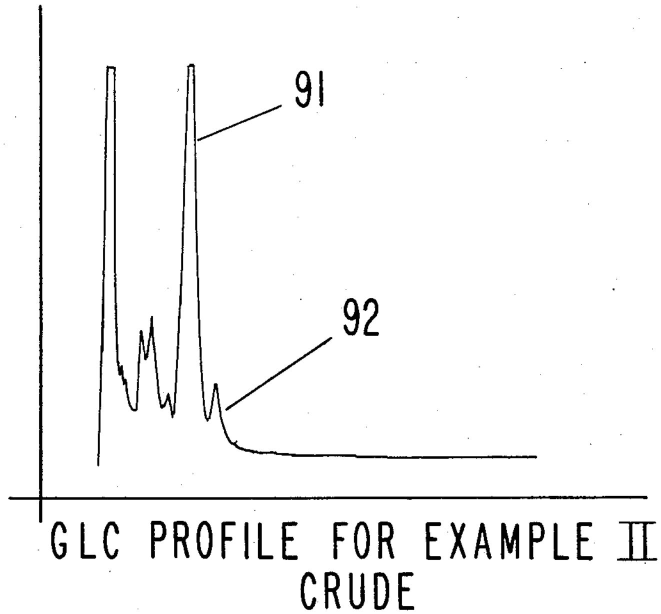
GLC PROFILE FOR EXAMPLE II .
CRUDE
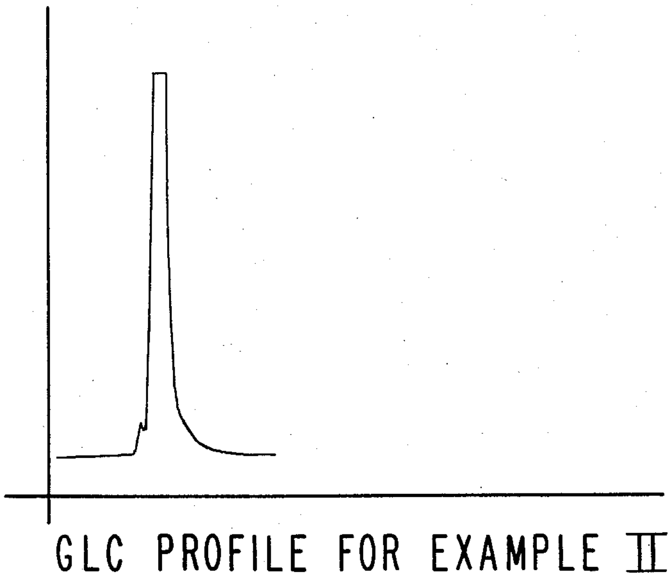
GLC PROFILE FOR EXAMPLE II ,
BULKED FRACTIONS 10-14 .
FIG.10

NMR SPECTRUM FOR PEAK "91" OF FIG.9, EXAMPLE II.

I R SPECTRUM FOR PEAK "91" OF FIG.9 , EXAMPLE II.

NMR SPECTRUM FOR PEAK "92" OF FIG.9, EXAMPLE II.

IR SPECTRUM FOR PEAK "92" OF FIG. 9, EXAMPLE II.

OXOBICYCLONONANE DERIVATIVES, PROCESS FOR PRODUCING SAME AND ORGANOLEPTIC USES THEREOF

BACKGROUND OF THE INVENTION

This invention relates to oxobicyclononane derivatives defined according to the structure:

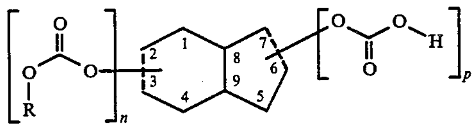

wherein R represents methyl or ethyl; one of the dashed lines represents a carbon-carbon single bond or a carbon-carbon double bond; N and P each represents 0 or 1; the sum of N and P being equal to 1; with the proviso that when N is 1, the dashed line at the "2-3" position is a carbon-carbon single bond and the dashed line at the "6-7" position is a carbon-carbon double bond and uses thereof in augmenting or enhancing the aroma of perfume compositions, colognes and perfumed articles.

Also covered by this invention are the precursor formates defined according to the structure:

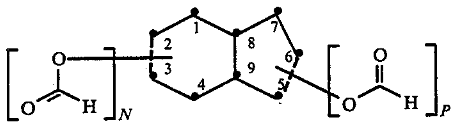

wherein the dashed lines, N and P are defined, supra.

Materials which can provide strawberry aromas with green banana topnotes are highly desirable in the art of perfumery. Many of the natural substances which provide such fragrance nuances and contribute the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

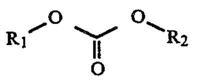

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having a herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

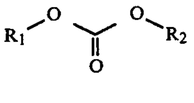

according to the reaction:

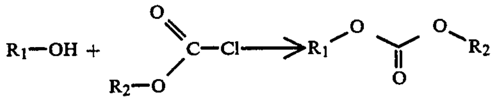

wherein $R_1$ and $R_2$ are defined as above.

In addition, U.S. Pat. No. 4,080,309 describes the perfume use of the carbonates defined according to the structure:

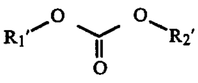

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of 4,080,309 are indicated to be prepared according to the reaction:

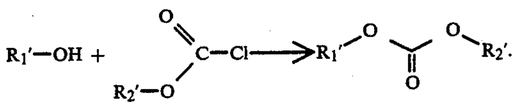

4-Cyclooctenyl alkyl carbonates defined according to the structure:

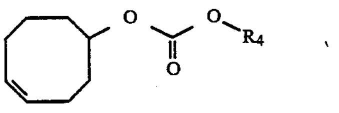

wherein $R_4$ is methyl or ethyl and reaction products including a major proportion of said 4-cyclooctenyl alkyl carbonates and a minor proportion of bicyclooctanyl carbonates having the structure:

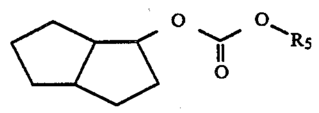

wherein $R_5$ is methyl or ethyl and uses thereof in augmenting or enhancing the aroma of perfume compositions, colognes and perfumed articles are described in U.S. Pat. No. 4,452,730 issued on June 5, 1984.

Tricyclodecane carbonates having the structures:

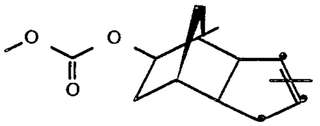

and

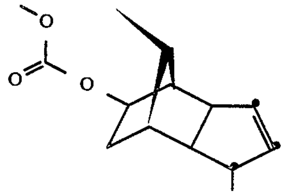

are described as having fruity (apple), anisic-like aromas with dry, hay-like and berry-like undertones.

However, nothing in the prior art describes the oxobicyclononane derivatives of our invention or the organoleptic utilities thereof.

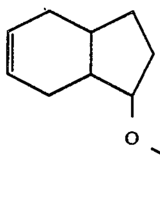

;

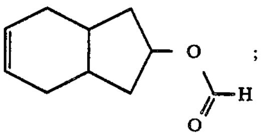

;

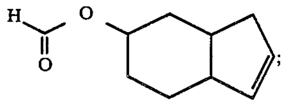

;

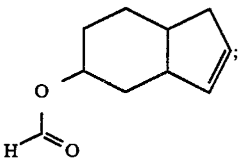

; and

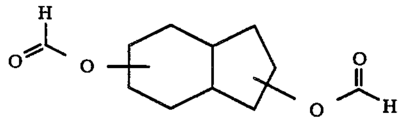

(Conditions: 6'×0.25" 10% SE-30 column programmed at 220° C. isothermal).

Figure 2:
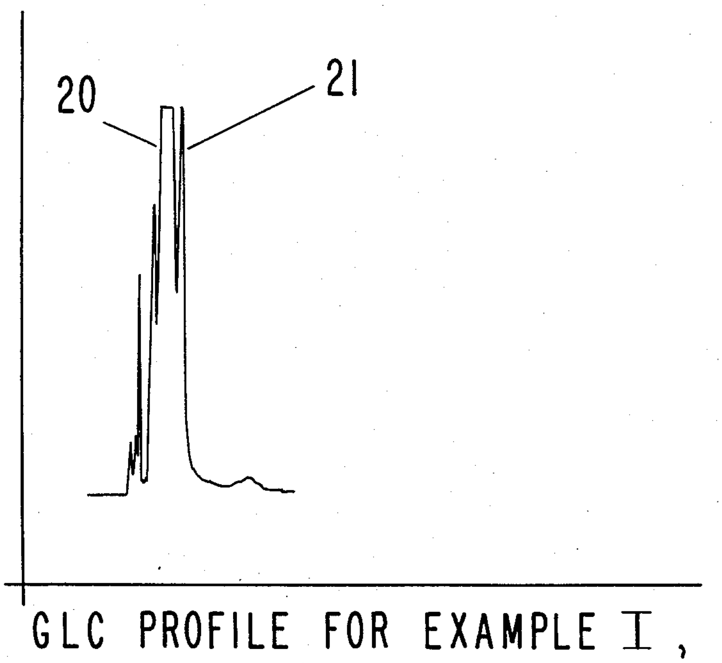

FIG. 2 is the GLC profile for bulked distillation Fractions 4–7 of the reaction product of Example I containing the compounds having the structures:

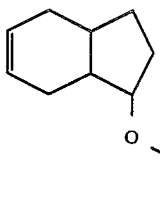

;

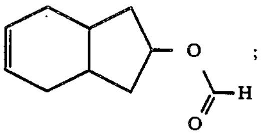

;

-continued

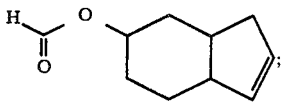

; and

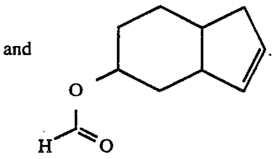

Figure 3:
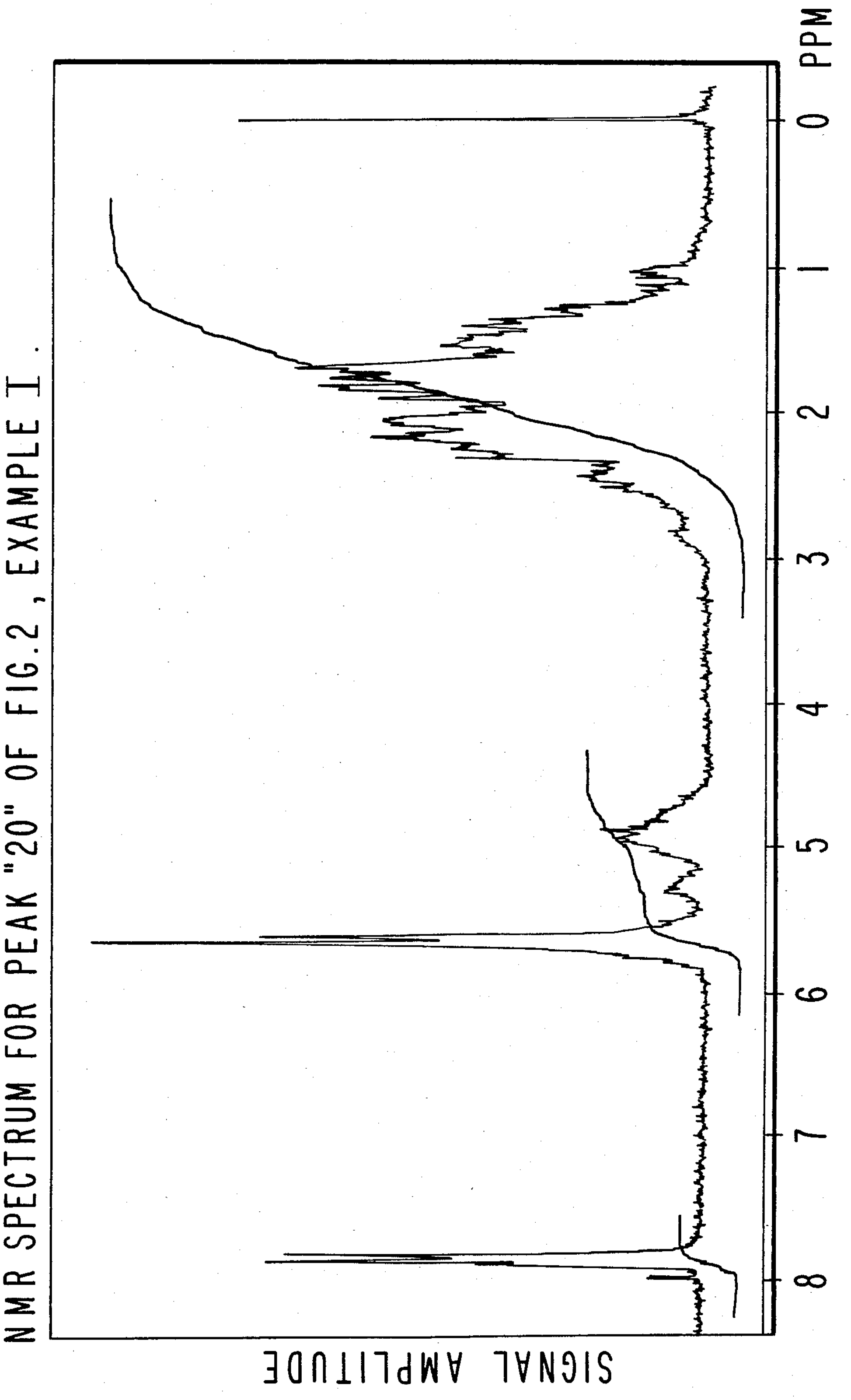

FIG. 3 is the NMR spectrum for the peak indicated by reference numeral 20 on the GLC profile of FIG. 2 containing the compounds having the structures:

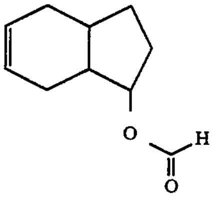

and

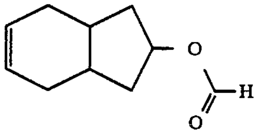

(Conditions: Field strength: 100 MHz; Solvent: $CFCl_3$).

Figure 4:
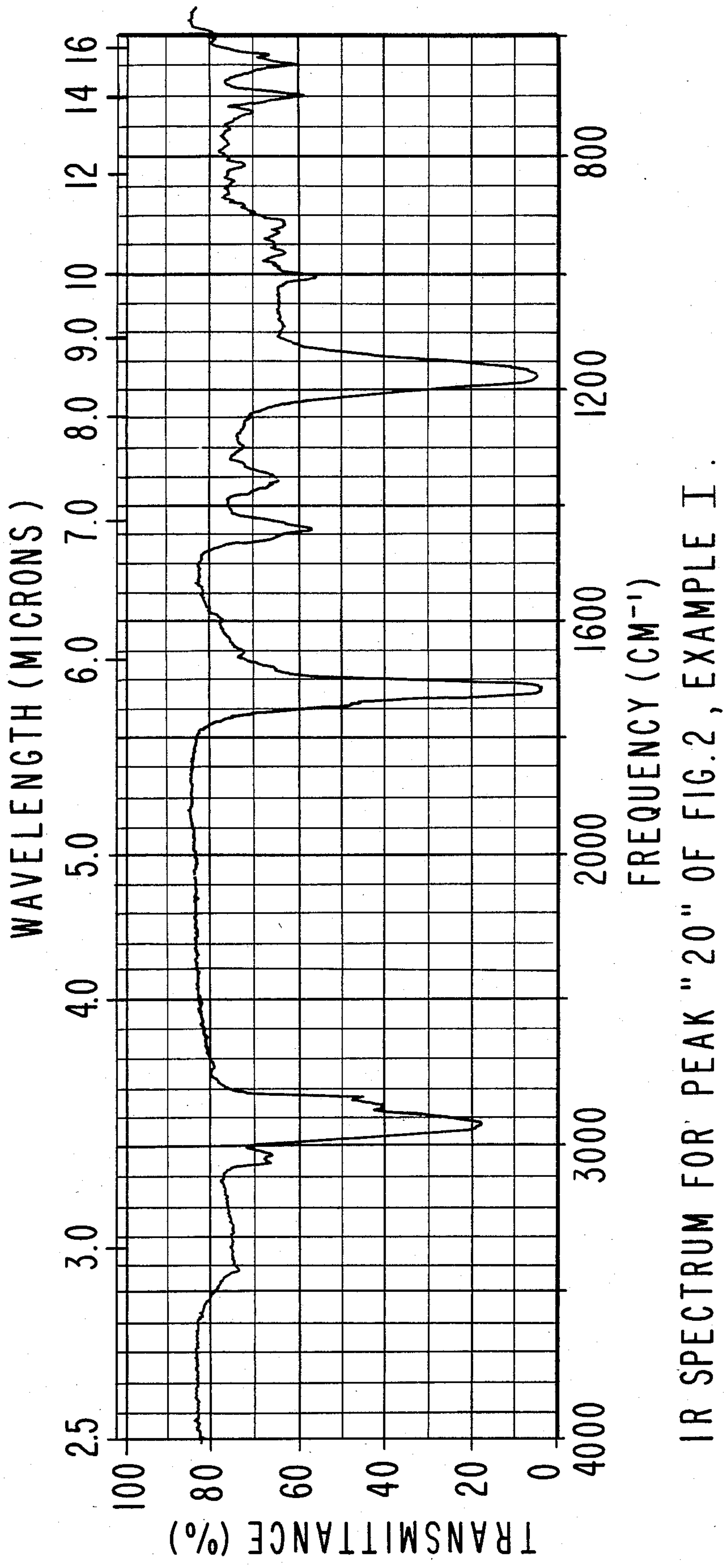

FIG. 4 is the infra-red spectrum for the peak indicated by reference numeral 20 on the GLC profile of FIG. 2 containing the compounds having the structures:

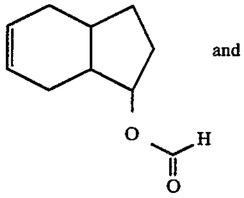

and

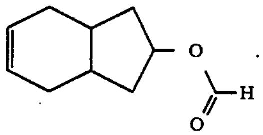

.

Figure 5:
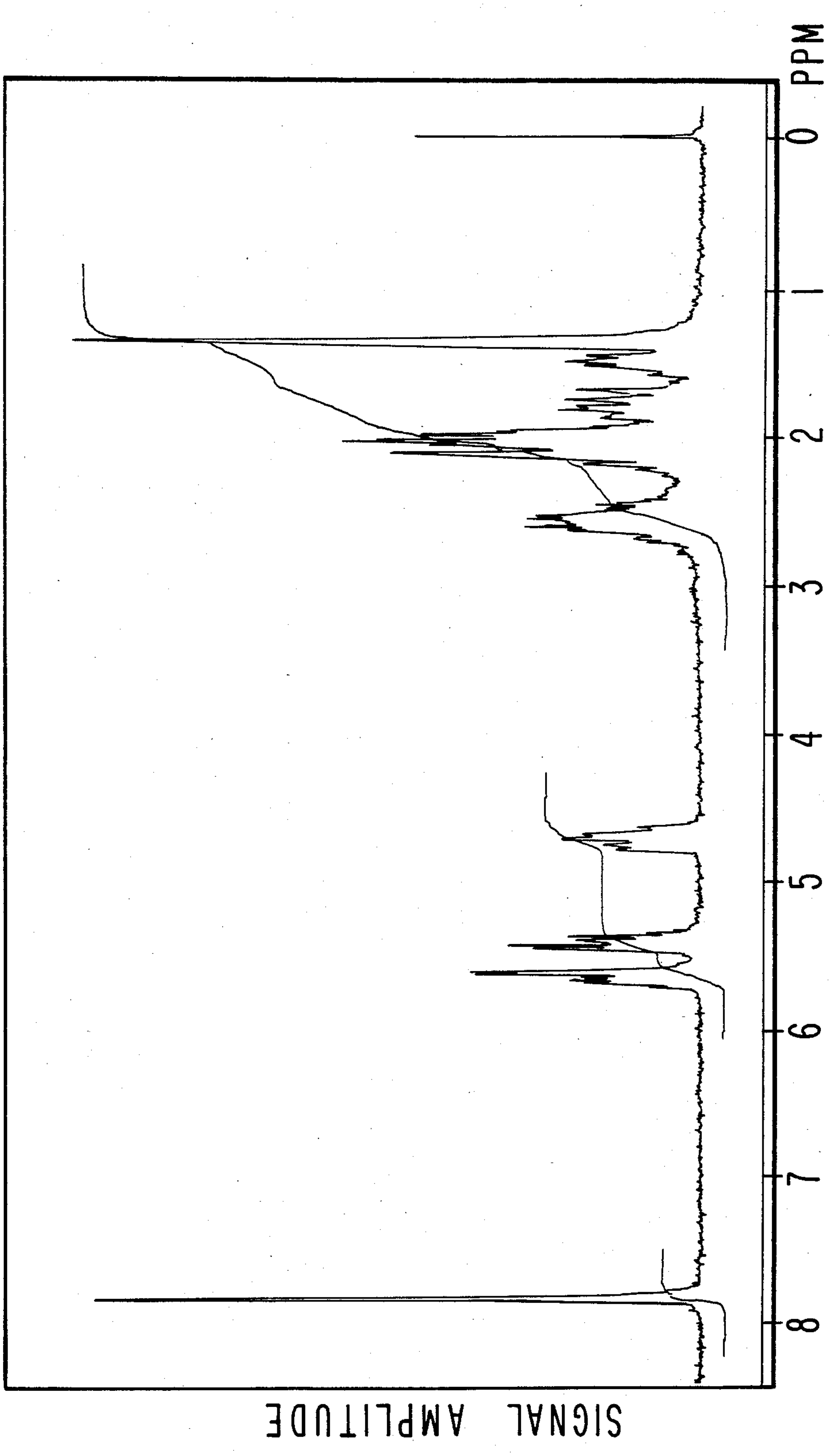

FIG. 5 is the NMR spectrum for the peak indicated by reference numeral 21 on the GLC profile of FIG. 2 containing the compounds having the structures:

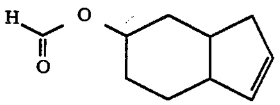

and

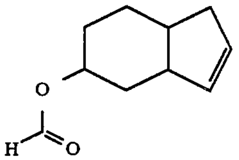

prepared according to Example I (Conditions: Field strength: 100 MHz; Solvent: $CFCl_3$).

Figure 6:
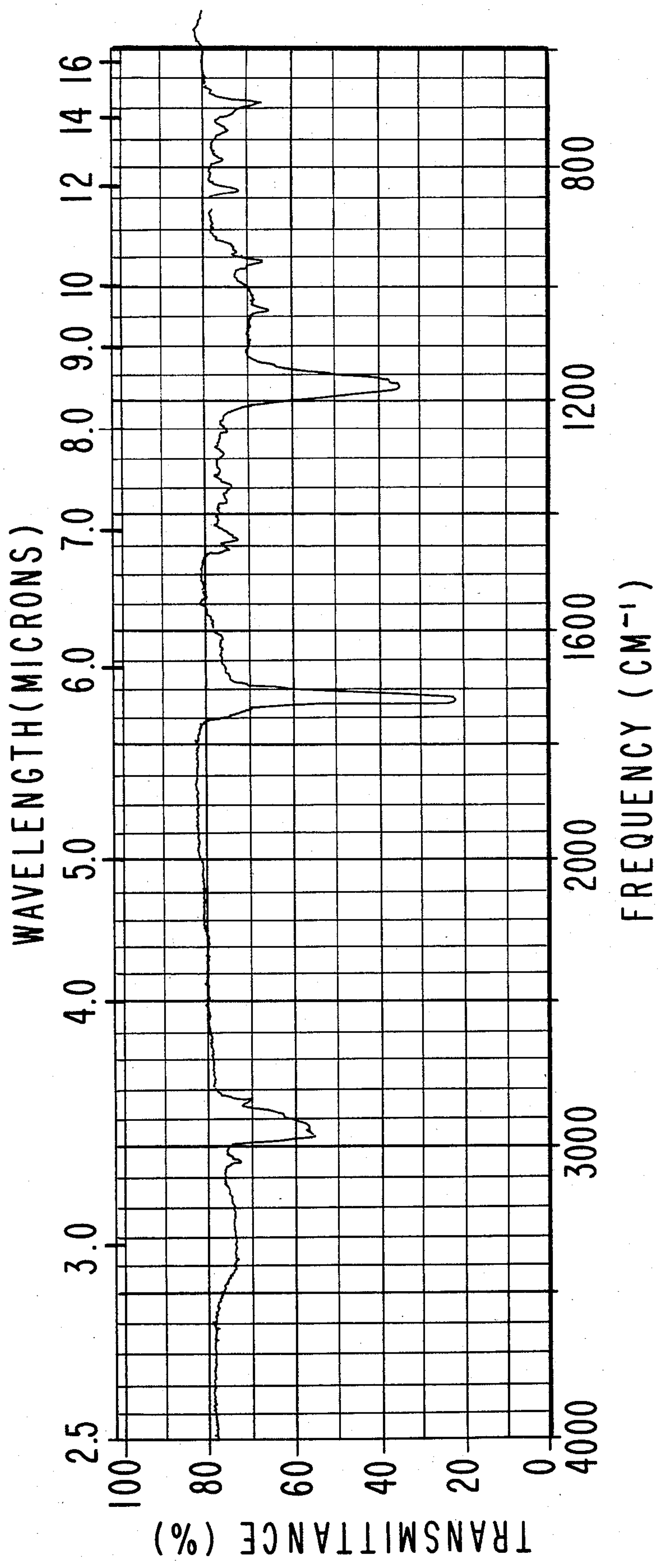

FIG. 6 is the infra-red spectrum for the peak indicated by reference numeral 21 on the GLC profile of FIG. 2 for the compounds having the structures:

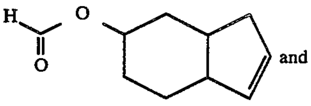

and

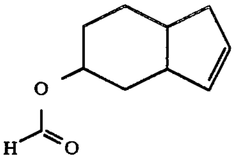

produced according to Example I.

Figure 1:
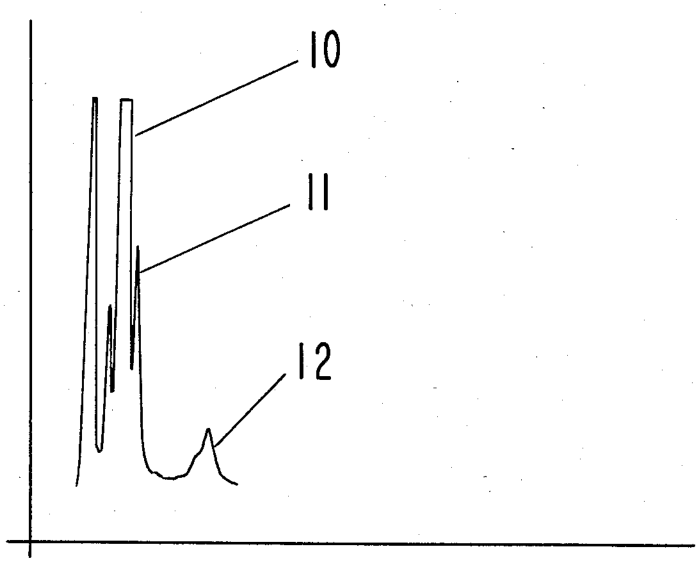
FIG. 1 is the GLC profile for the crude reaction product of Example I containing the mixture of compounds having the structures.
Figure 7:
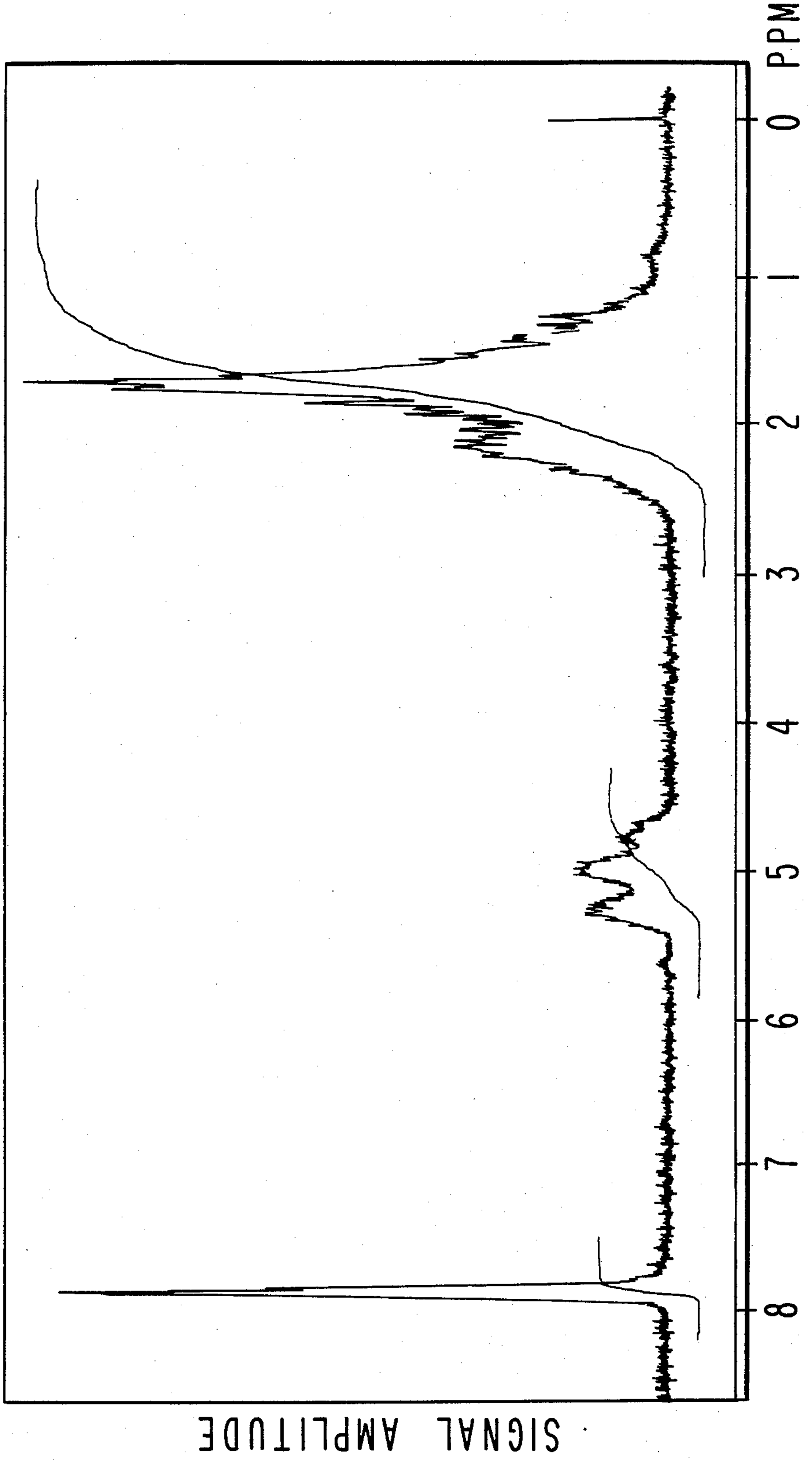

FIG. 7 is the NMR spectrum for the peak indicated by reference numeral 12 on the GLC profile for FIG. 1 prepared according to Example I containing the mixture of compounds having the structure:

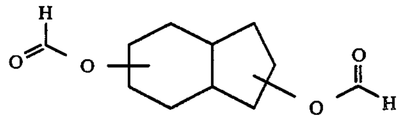

(Conditions: Field strength: 100 MHz; Solvent: $CFCl_3$).

Figure 8:
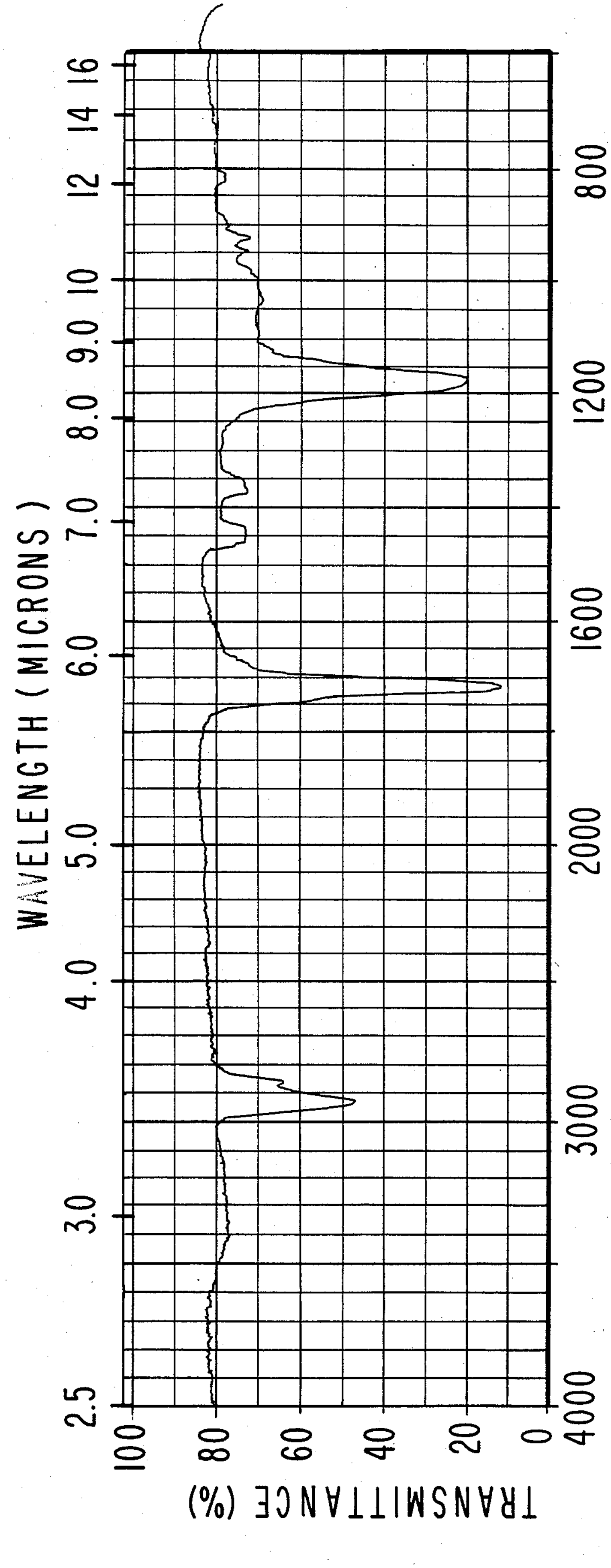

FIG. 8 is the infra-red spectrum for the peak indicated by reference numeral 12 of the GLC profile of FIG. 1 for the mixture of compounds having the structure:

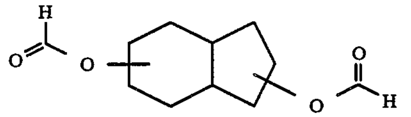

prepared according to Example I.

FIG. 9 is the GLC profile for the crude reaction product of Example II containing the compounds having the structures:

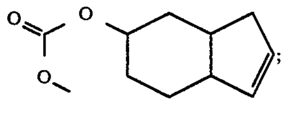
;

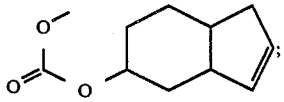
;

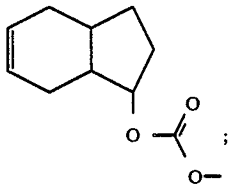
; and

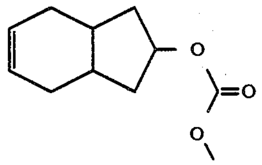

FIG. 10 is the GLC profile for bulked distilation Fractions 10-14 of the distillation of the reaction product of Example II containing the compounds having the structures:

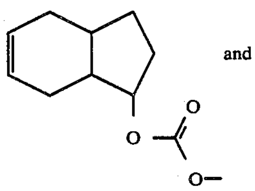
and
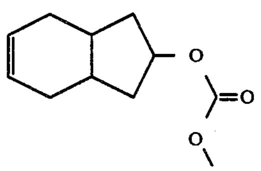

prepared according to Example II (Conditions: 6'×0.25% 10% SE-30 column programmed at 220° C. isothermal).

Figure 11:
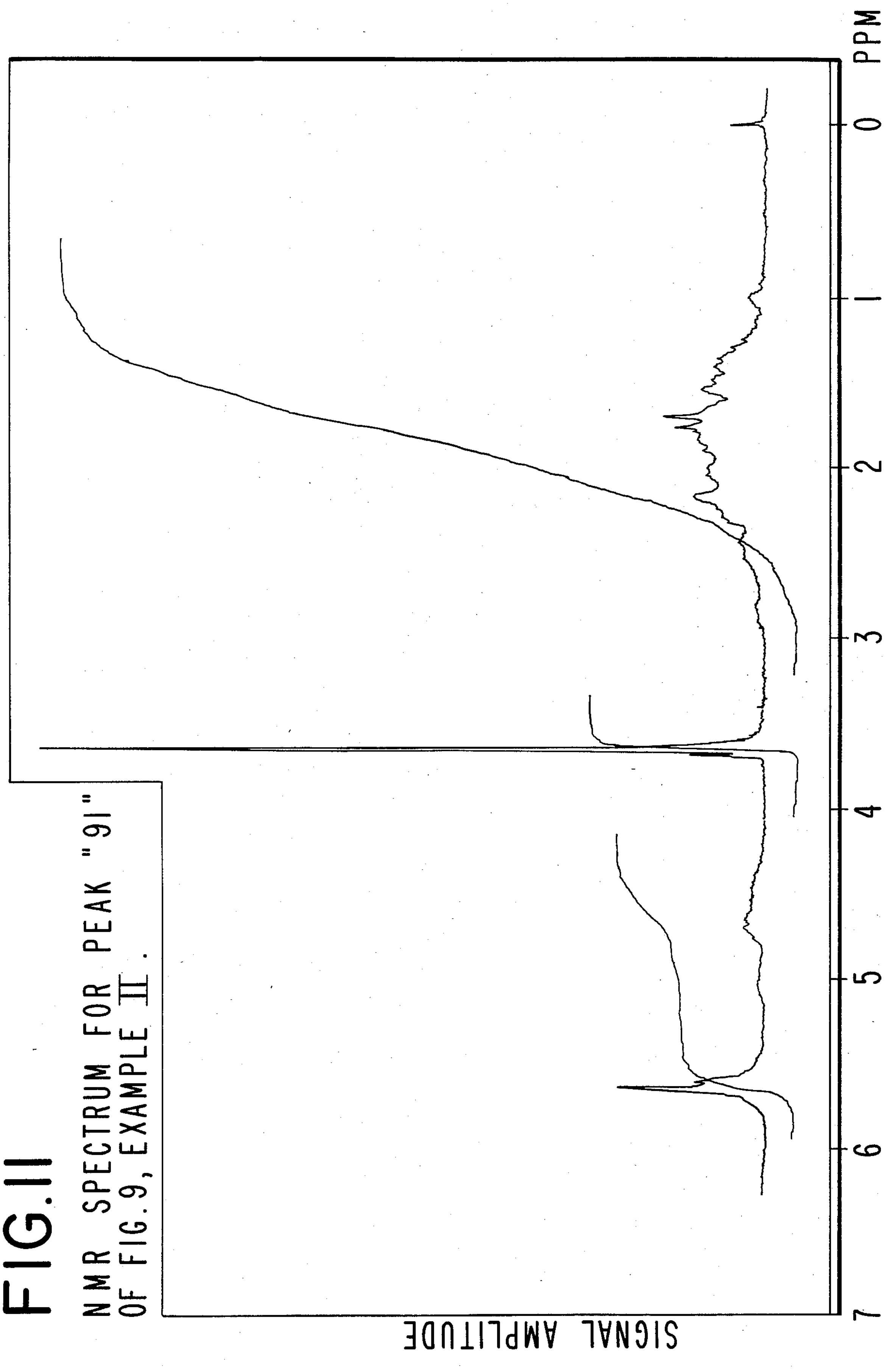

FIG. 11 is the GLC profile for the peak indicated by reference numeral 91 on the GLC profile of FIG. 9 containing the compounds having the structures:

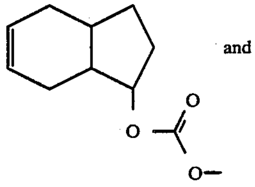
and
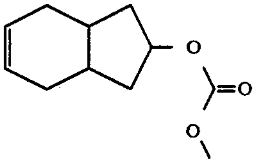

prepared according to Example II (Conditions: Field strength: 100 MHz; Solvent: $CFCl_3$).

Figure 12:
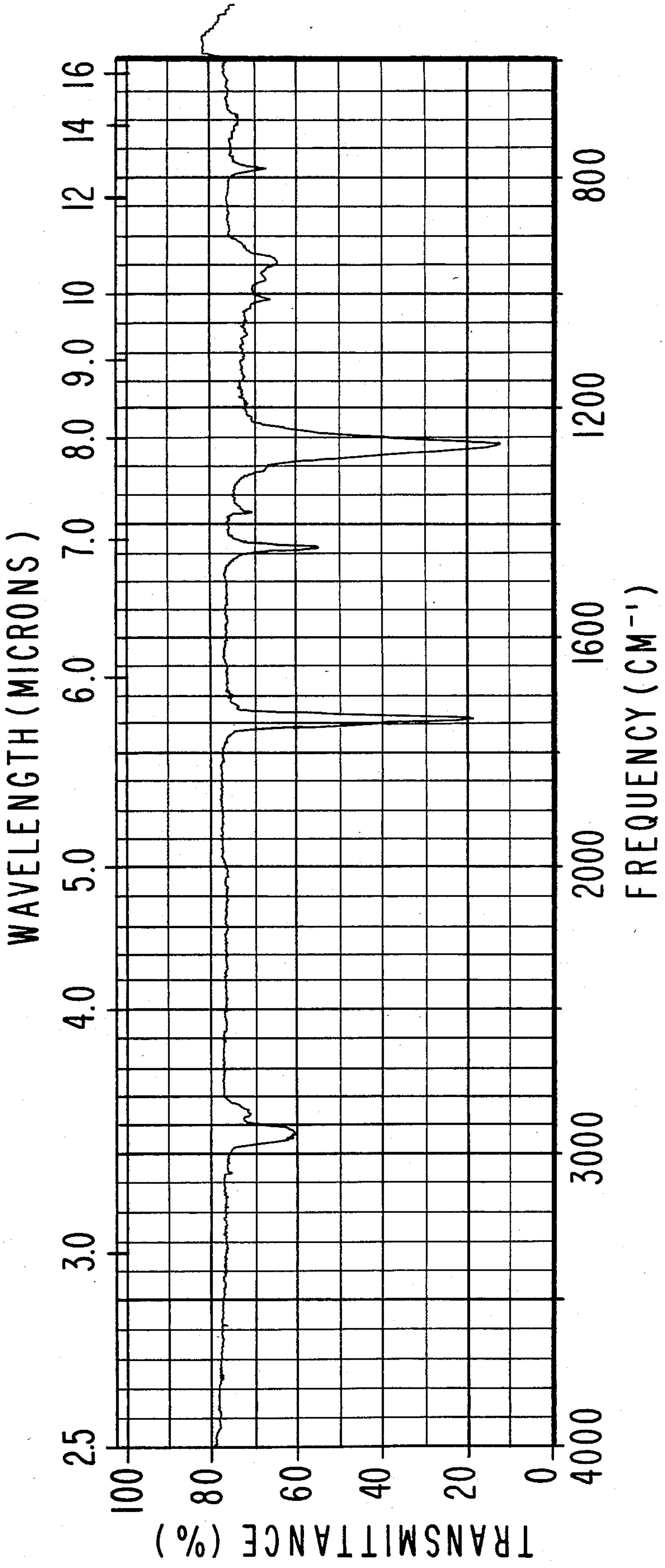

FIG. 12 is the infra-red spectrum for the peak indicated by reference numeral 91 on the GLC profile of FIG. 9 containing the compounds having the structures:

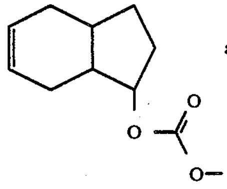
and
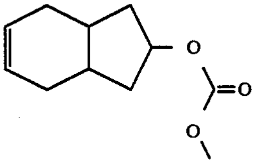

prepared according to Example II.

Figure 13:
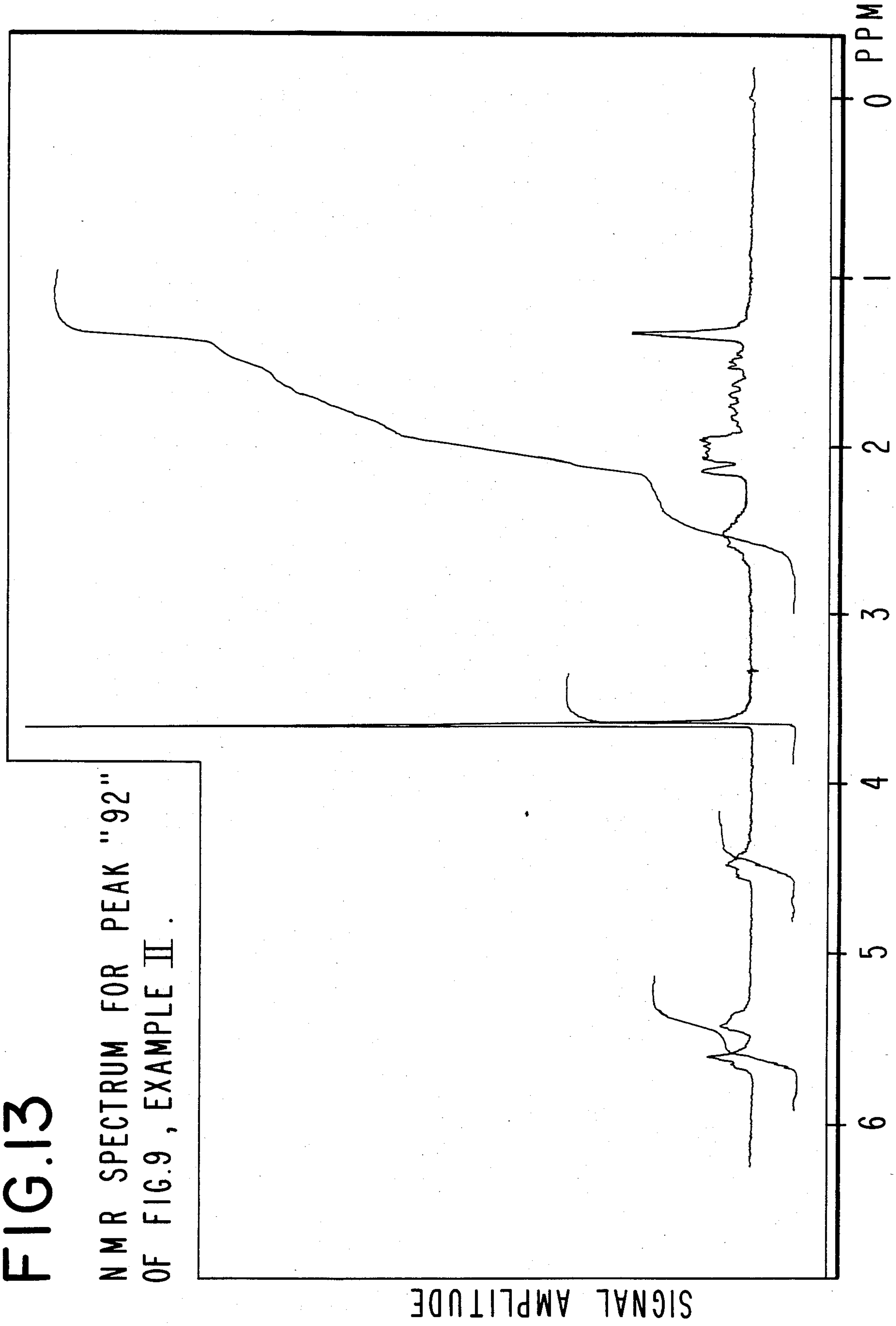

FIG. 13 is the NMR spectrum for the peak indicated by reference numeral 92 on the GLC profile of FIG. 9 containing the compounds having the structures:

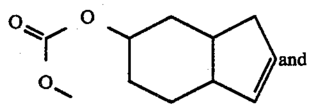
and
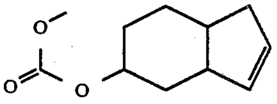

prepared according to Example II (Conditions: Field strength: 100 MHz; Solvent: $CFCl_3$).

Figure 14:
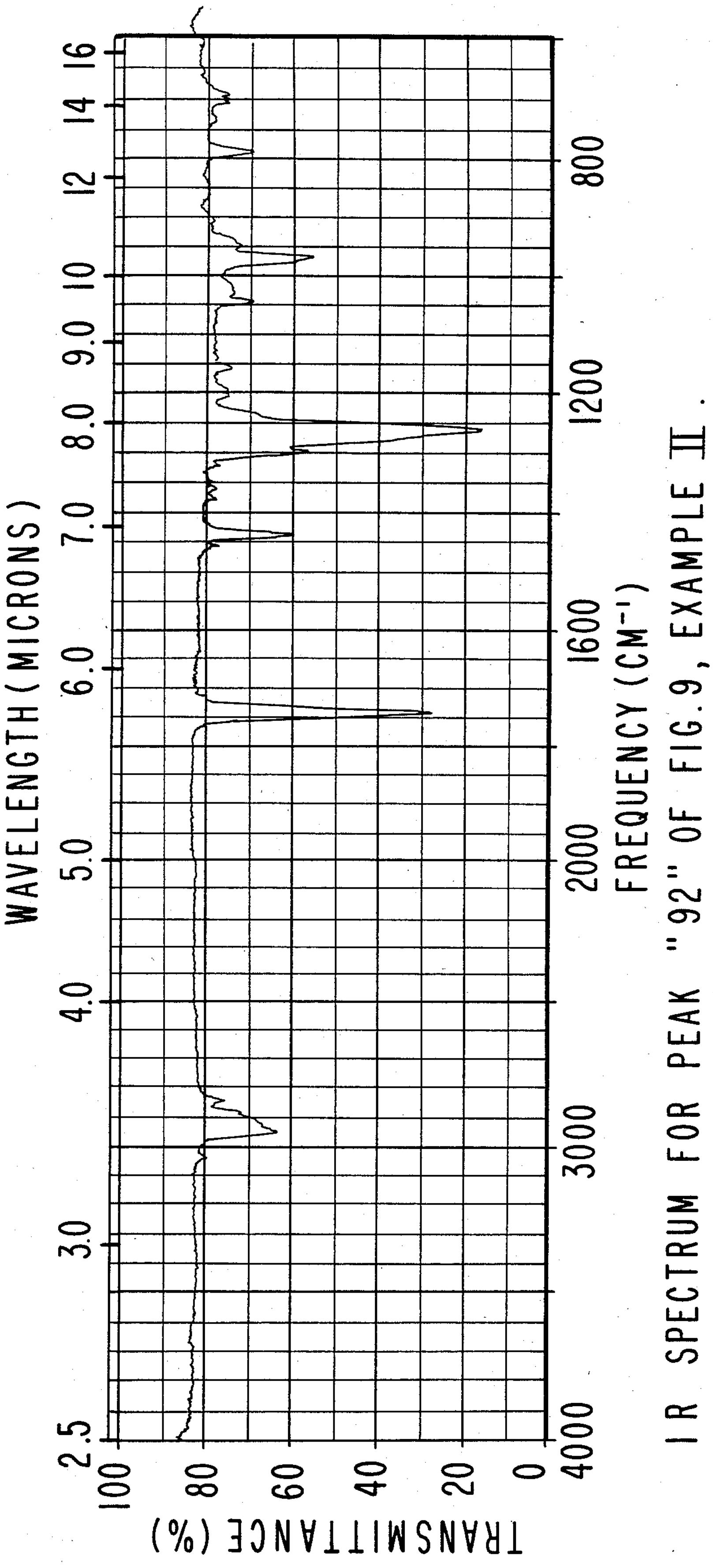

FIG. 14 is the infra-red spectrum for the peak indicated by reference numeral 92 on the GLC profile of FIG. 9 containing the compounds having the structures:

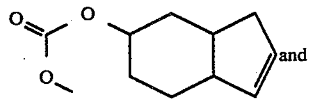
and
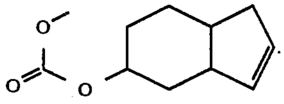
.

DETAILED DESCRIPTION OF THE DRAWINGS

FIG. 1 is the GLC profile for the crude reaction product of Example I (Conditions: 6'×0.25" 10% SE-30 column programmed at 220° C. isothermal). The peak indicated by reference numeral 10 is the peak for the compounds having the structures:

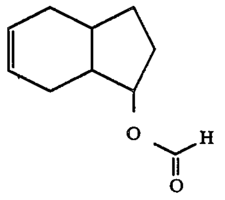

and

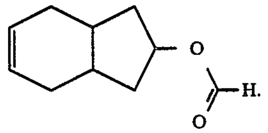

The peak indicated by reference numeral 11 is the peak for the compounds having the structures:

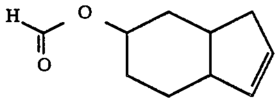

and

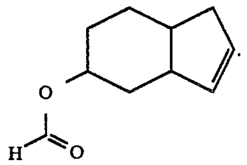

The peak indicated by reference numeral 12 is the peak for the mixture of compounds having the structure:

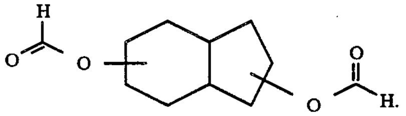

FIG. 2 is the GLC profile for bulked distillation Fractions 4–7 of the reaction product of Example I (Conditions: 6'×0.25" 10% SE-30 column programmed at 220° C. isothermal).

The peak indicated by reference numeral 20 is the peak for the compounds having the structures:

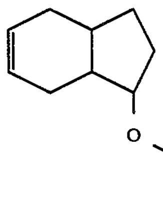

and

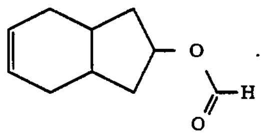

The peak indicated by reference numeral 21 is the peak for the compounds having the structures:

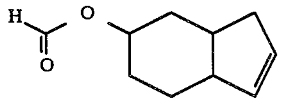

and

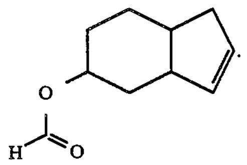

FIG. 9 is the GLC profile of the crude reaction product of Example II. The peak indicated by reference numeral 91 is the peak for the compounds having the structures:

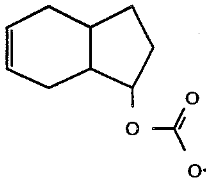

and

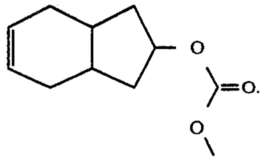

The peak indicated by reference numeral 92 is the peak for the compounds having the structures:

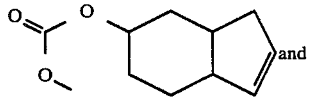

and

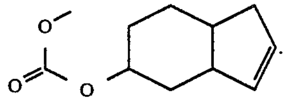

THE INVENTION

The present invention provides compounds having the structure:

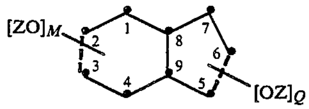

wherein Z represents alkoxy carbonyl or formyl; wherein one of the dashed lines represents a carbon-carbon double bond and the other of the dashed lines represents a carbon-carbon single bond; wherein M and Q each represents 0 or 1 with the proviso that the sum of M+Q is 1 and with the further proviso that M is 1 when the dashedd line at the "2-3" position is a carbon-carbon single bond and the dashed line at the "5-6" position is a carbon-carbon double bond and Q is 1 when the dashed line at the "5-6" position is a carbon-carbon single bond and the dashed line at the "2-3" position is a carbon-carbon double bond including the genuses having the structures:

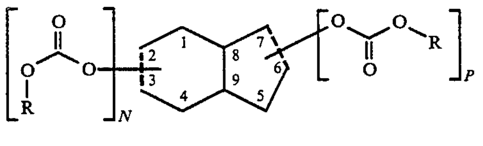

and

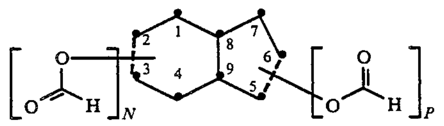

wherein R represents methyl or ethyl; N and P each represents 0 or 1; each of the dashed lines represents a carbon-carbon single bond or a carbon-carbon double bond with the provisos:

(i) the sum of N+P=1;

(ii) when N is 1 the dashed line at the "2-3" position is a carbon-carbon single bond and the dashed line at the "6-7" position is a carbon-carbon double bond and when P is 1 the dashed line at the "6-7" position is a carbon-carbon single bond and the dashed line at the "2-3" position is a carbon-carbon double bond.

The compounds covered by the genus having the structure:

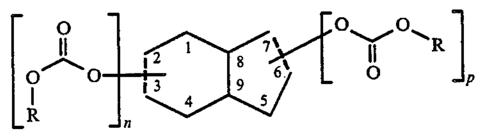

(carbonates) have utilities in perfumery; that is, in augmenting or enhancing the aroma of perfume compositions, colognes and perfumed articles including solid or liquid anionic, cationic, nonionic or zwitterionic detergents, fabric softener compositions, fabric softener articles, cosmetic compositions, hair preparations and perfumed polymers. The compounds covered by the genus having the structure:

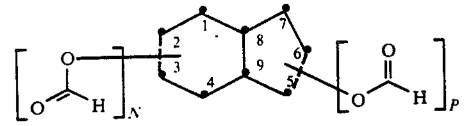

are useful as intermediates or precursors in forming the genus having the structure:

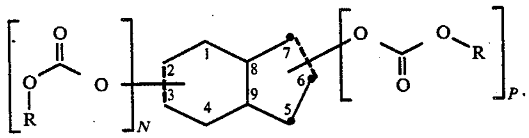

The compounds defined according to the genus:

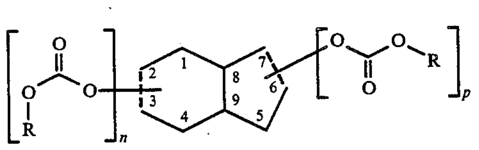

have a strawberry aroma with green banana topnotes.

The present invention also provides an economically efficient process for synthesizing the compounds defined according to the structure:

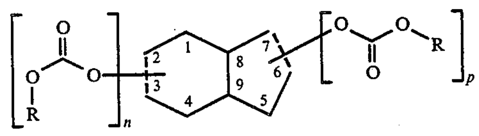

by first reacting bicyclononadiene having the structure:

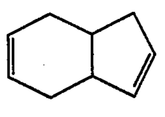

with formic acid according to the reaction:

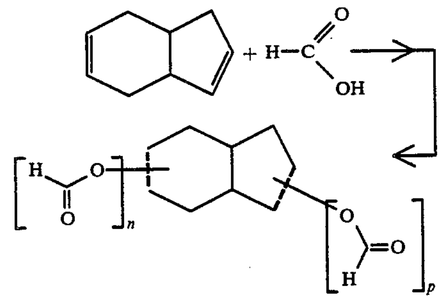

and then reacting the resulting formate compound with the carbonate having the structure:

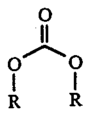

(wherein R represents methyl or ethyl) according to the reaction:

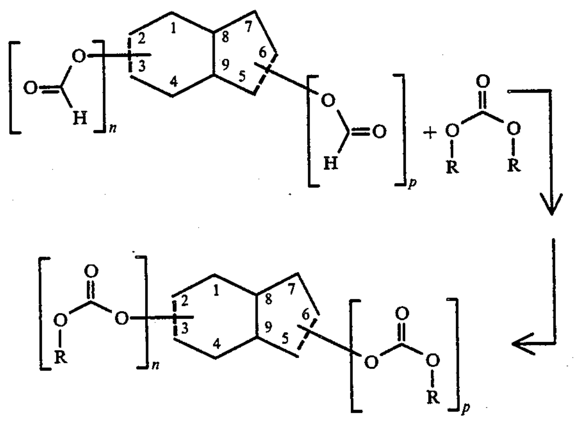

The bicyclononene formate is formed from bicyclononadiene by reaction of bicyclononadiene with formic acid. The reaction is carried out at reflux conditions for a period sufficient to yield a product containing greater than 80% bicyclononene formate. The mole ratio of formic acid:bicyclononadiene may vary between about 2:1 up to about 7:1 with a preferred mole ratio of between 5.5:1 and 6:1 of formic acid:bicyclononadiene. At the end of the reaction the reaction product, the bicyclononene formate is distilled. The crude reaction product contains the compounds having the structures:

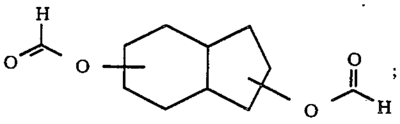
;
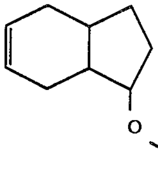
;
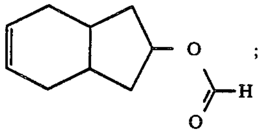
;
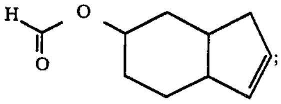
; and
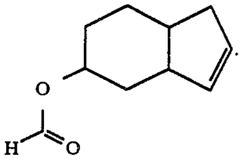

with the majority of the mixture being the compounds having the structures:

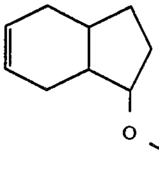
and
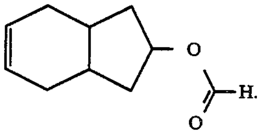

The compound having the structure:

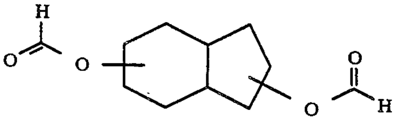

is separated out from the reaction mass by fractional distillation leaving the compounds having the structures:

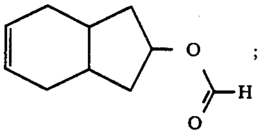
;
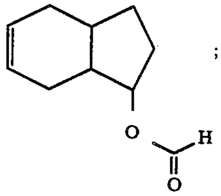
;
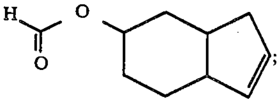
; and
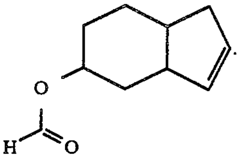

These compounds may be separated from one another whereby the group of compounds having the structures:

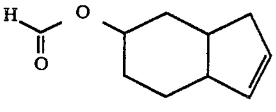
and
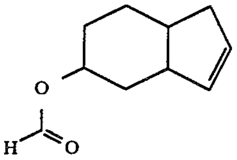

may be separated from the group of compounds having the structures:

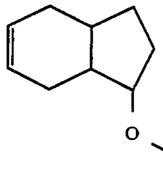
and
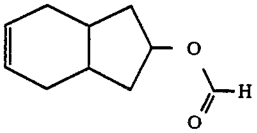

by preparative liquid chromatography. However, from a practical standpoint the fractional distillation product is sufficient for the purposes of use of the resulting bicyclononenyl formates as intermediates in preparing carbonates which are subsequently useful in perfumary.

The resulting mixture of compounds having the structures:

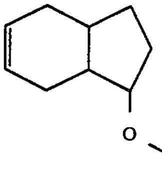
;
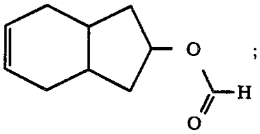
;
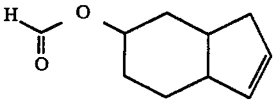
and
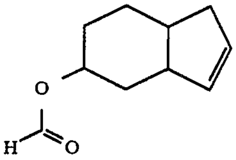

is then reacted with either diethyl carbonate or dimethyl carbonate defined according to the structure:

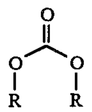

wherein R represents methyl or ethyl in the presence of an alkali metal alkoxide catalyst such as sodium methoxide, sodium ethoxide, sodium isopropoxide, potassium t-butoxide as well as other metal alkoxides such as aluminum isopropoxide. The reaction temperature may vary between 50° C. and 90° C. with a preferred reaction temperature of between 60° and 80° C.

The mole ratio of dialkyl carbonate to bicyclononenyl formate may vary from about 2:1 up to about 4:1 with a preferred mole ratio of about 2.8:1. The concentration of alkali metal alkoxide or other metal alkoxide in the reaction mass may vary from about 0.03 moles per liter up to about 0.5 moles per liter with a preferred concentration of alkali metal alkoxide or other metal alkoxide in the reaction mass being about 0.05 moles per liter. At the end of the reaction the reaction mass is quenched with weak acid such as acetic acid. The reaction mass is then fractionally distilled thereby recovering a mixture of carbonates having the structures:

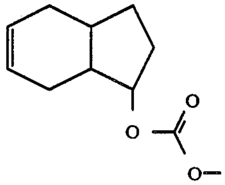
and
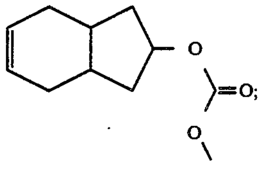
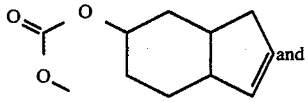
and
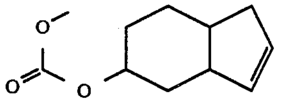

with the major (e.g., greater than 75%) portion of carbonates having the structures:

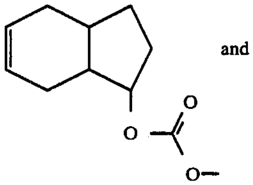
and
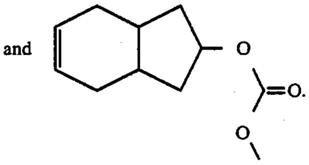

The group of carbonates having the structures:

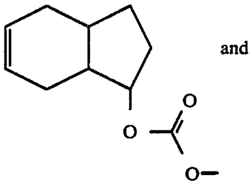
and
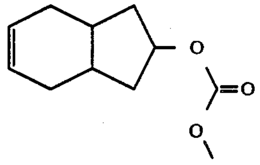

may be separated by preparative liquid chromatography from the group of carbonates having the structures:

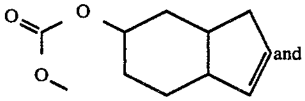
and

-continued

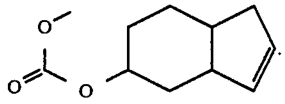

However from a practical standpoint it is preferable not to so separate the fractional distillation products but to use such fractional distillation products "as is" for their organoleptic properties in perfumery, e.g., augmenting or enhancing the aroma of perfume compositions, perfumed articles and colognes.

As stated, supra, the oxobicyclononane derivatives of our invention can be used to contribute strawberry aromas with green banana topnotes to perfume compositions, perfumed articles and colognes with the perfumed articles being such materials as solid or liquid anionic, cationic, nonionic or zwitterionic detergents, perfumed polymers, fabric softener compositions, fabric softener articles, optical brighteners, fabric conditioners, hair preparations, shampoos and hair sprays. As olfactory agents the oxobicyclononane derivatives of our invention can be formulated into or used as components of a "perfume composition".

The term "perfume composition" is used herein to mean a mixture of organic compounds including, for example, alcohols, aldehydes, ketones, nitriles, ethers, lactones, esters other than the carbonates of our invention and frequently, hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of oxobicyclononane derivative(s) of our invention which will be effective in perfume compositions depends upon many factors including the other ingredients, their amounts and the effects which are desired. It has been found that perfume compositions containing as little as 0.1% of the oxobicyclononane derivative(s) of our invention or even less and perfume compositions containing as much as 70% of one or more of the oxobicyclononane derivative(s) of our invention can be used to impart interesting, strawberry-like aromas with green banana topnotes to perfumed articles, perfume compositions and colognes. Such perfumed articles include fabric softener compositions, drier-added fabric softener articles, cosmetic powders, talcs, solid or liquid anionic, cationic, nonionic or zwitterionic detergents and perfumed polymers. The amount employed an range up to 70% as stated, supra and will depend on considerations of cost, nature of the end product and the effect desired on the finished product and particular fragrance sought.

Thus, one or more of the oxobicyclononane derivative(s) of our invention can be used alone or in a perfume composition as an olfactory component, in solid or liquid anionic, cationic, nonionic or zwitterionic detergents (including hand soaps) perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler or such as a solid or liquid cationic, anionic, nonionic or zwitterionic detergent or of a cosmetic powder, as little as 0.01% of one or more of the oxobicyclononane derivative(s) of our invention will suffice to provide an interesting strawberry-like aroma with green banana topnotes. Generally, no more than 0.8% of one or more of the oxobicyclononane derivative(s) of our invention is required. Thus, the range of oxobicyclononane derivative(s) in perfumed articles may vary from about 0.01% up to about 0.8%.

In addition, the perfume compositions of our invention can contain a vehicle or carrier for the oxobicyclononane derivative(s) of our invention alone or with other ingredients. The vehicle can be a liquid such as an alcohol such as ethanol, a glycol such as propylene glycol or the like. The carrier can be an absorbent solid such as a gum (e.g., xanthan gum or gum arabic) or components for encapsulating the composition as by coacervation using gelatin or by forming a polymeric shell around a liquid perfume center by means of the use of a urea formaldehyde prepolymer.

The following Examples I and II set forth processes for preparing the oxobicyclononane derivatives of our invention Examples following Example II set forth methods for using the oxobicyclononane derivatives of our invention for their organoleptic properties.

Unless otherwise indicated, all parts and percentages are by weight.

EXAMPLE I

Preparation of Mixture Containing Bicyclonenyl Formate Compounds

Reaction:

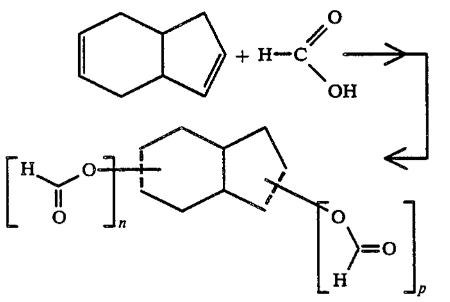

Into a 500 cc reaction flask equipped with stirrer, thermometer, heating mantle and reflux condenser are placed 120 grams (1 mole) of bicyclononadiene having the structure:

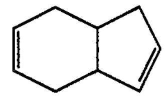

and 261 grams (5.7 moles) of formic acid wherein a mixture is formed containing several compounds and wherein in the mixture N and P each represents 0 or 1 and wherein the dashed lines represent carbon-carbon single bonds or carbon-carbon double bonds with the proviso that when N is 1 and P is 1, both of the dashed lines represent carbon-carbon single bonds.

The reaction mass is then refluxed at 100° C. for a period of 9 hours. At the end of the 9 hour period, a 10% sodium chloride solution is added to the reaction mass. The organic phase is separated from the aqueous phase and the organic phase is distilled yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 25/53 | 40/68 | 38/38 | 200 |
| 2 | 60 | 73 | 2.4 | 89 |
| 3 | 70 | 83 | 2.4 | 102 |
| 4 | 74 | 84 | 2.0 | 102 |
| 5 | 76 | 86 | 2.0 | 97 |
| 6 | 86 | 110 | 2.0 | 242 |
| 7 | 86 | 120 | 2.0 | 257 |
| 8 | 120 | 150 | 2.0 | 62 |
| 9 | 150 | 195 | 2.0 | 94 |
| 10 | 173 | 245 | 2.4 | 65 |

The distillation is carried out on a 2" splash column.

FIG. 1 is the GLC profile of the crude reaction product prior to distillation. The peak indicated by reference numeral 10 is the peak for the mixture of compounds having the structures:

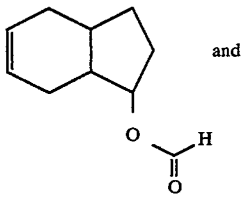

and

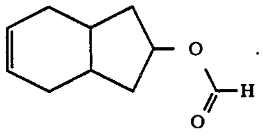

The peak indicated by reference numeral 11 is the peak for the mixture of compounds having the structures:

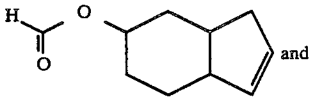

and

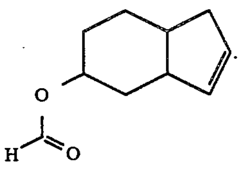

The peak indicated by reference numeral 12 is the peak for the mixture of compounds having the structure:

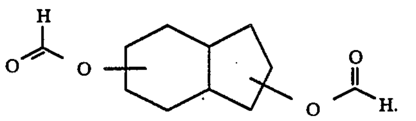

FIG. 2 is the GLC profile for bulked distillation Fractions 4–7 of the foregoing distillation. The peak indicated by reference numeral 20 is the peak for the mixture of compounds having the structures:

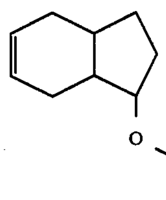

and

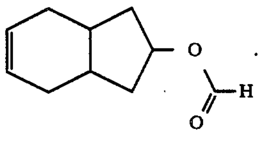

The peak indicated by reference numeral 21 is the peak for the mixture of compounds having the structures:

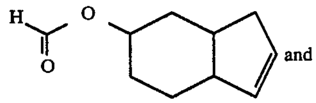

and

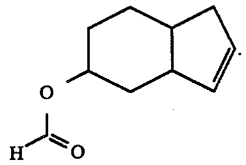

FIG. 3 is the NMR spectrum for the peak indicated by reference numeral 20 of FIG. 2 for the compounds having the structures:

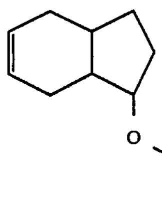

and

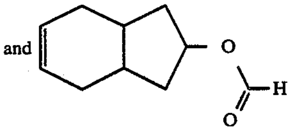

(Conditions: Field strength: 100 MHz; Solvent: $CFCl_3$).

FIG. 4 is the infra-red spectrum for the peak indicated by reference numeral 20 of the GLC profile of FIG. 2 for the compounds having the structures:

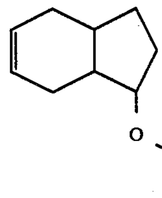

and

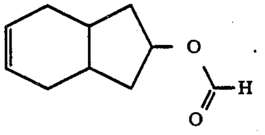

FIG. 5 is the NMR spectrum for the peak indicated by reference numeral 21 of the GLC profile of FIG. 2 for the mixture of compounds having the structures:

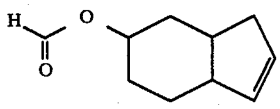

and

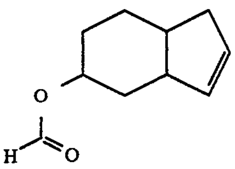

(Conditions: Field strength: 100 MHz; Solvent: $CFCl_3$).

FIG. 6 is the infra-red spectrum for the peak indicated by reference numeral 21 of the GLC profile of FIG. 2 for the mixture of compounds having the structures:

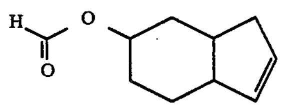

and

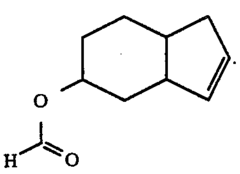

EXAMPLE II

Preparation of Bicyclononanyl Methyl Carbonate Mixture

Reaction:

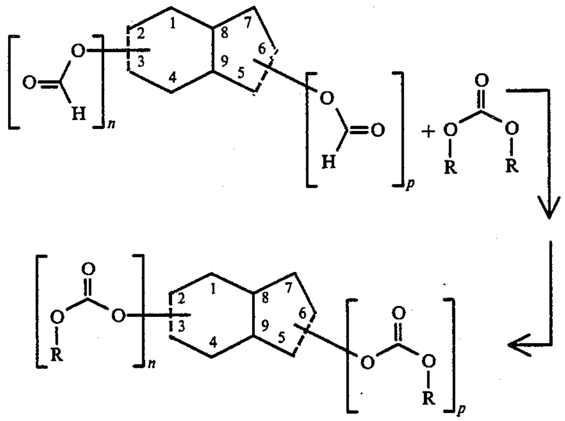

wherein R represents methyl; wherein in the compounds represented by the structures having dashed lines, these structures represent a mixture wherein one of the dashed lines represents a carbon-carbon double bond and the other of the dashed lines represents a carbon-carbon single bond; where N and P are 0 or 1 with the provisos that when N is 1, P is 0 and when N is 0, P is 1 and, further, when N is 1 the dashed line at the "2-3" position is a carbon-carbon single bond and the dashed line at the "5-6" position is a carbon-carbon double bond and when P is 1 the dashed line at the "5-6" position is a carbon-carbon single bond and the dashed line at the "2-3" position is a carbon-carbon double bond.

Into a 2 liter reaction vessel equipped with stirrer, thermometer and reflux condenser are placed 698 grams (3.9 moles) of bicyclononenyl formate produced according to Example I containing compounds having the structures:

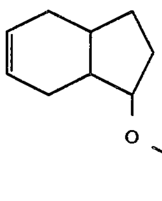
;
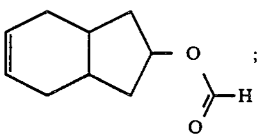
;
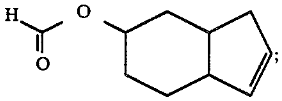
; and
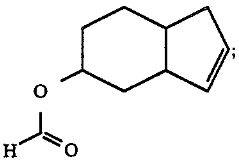
;

842 grams (9.3 moles) of dimethyl carbonate and 59 grams of 25% sodium methoxide in methyl alcohol (0.27 moles). The reaction mass is stirred at reflux for a period of 1 hour. After the 1 hour period, 24 grams (0.4 moles) of acetic acid is added to the reaction mass and stirring is continued for an additional 30 minutes.

The reaction product is then distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 43/78 | 50/102 | 2/1 | 95 |
| 2 | 98 | 100 | 1.0 | 163 |
| 3 | 105 | 104 | 1.0 | 101 |
| 4 | 108 | 114 | 1.0 | 258 |
| 5 | 108 | 140 | 1.0 | 123 |
| 6 | 200 | 220 | 1.0 | 88 |

Fractions 2, 3, 4 and 5 are bulked and the bulked fractions are redistilled on an 18" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 65/82 | 110/114 | 4/3.8 | 4:1 | 28 |
| 2 | 85 | 118 | 3.8 | 4:1 | 28 |
| 3 | 72 | 108 | 2.0 | 4:1 | 22 |
| 4 | 65 | 112 | 0.8 | 4:1 | 40 |
| 5 | 75 | 114 | 0.8 | 4:1 | 34 |
| 6 | 76 | 114 | 0.8 | 9:1 | 17 |
| 7 | 78 | 114 | 0.8 | 4:1 | 16 |
| 8 | 79 | 115 | 0.8 | 4:1 | 24 |
| 9 | 82 | 115 | 0.8 | 4:1 | 33 |
| 10 | 82 | 115 | 0.8 | 4:1 | 35 |
| 11 | 82 | 118 | 0.8 | 4:1 | 35 |
| 12 | 82 | 119 | 0.8 | 4:1 | 43 |
| 13 | 82 | 120 | 0.8 | 4:1 | 38 |
| 14 | 85 | 124 | 0.8 | 4:1 | 52 |
| 15 | 88 | 125 | 0.8 | 4:1 | 45 |
| 16 | 88 | 128 | 0.8 | 4:1 | 45 |
| 17 | 89 | 138 | 0.8 | 4:1 | 36 |
| 18 | 89 | 220 | 0.8 | 4:1 | 33 |

Fractions 8 to 17 of the foregoing distillations are bulked and indicated to have a very interesting, fruity, strawberry aroma with fresh, green, banana topnotes.

The resulting reaction product as confirmed by NMR, IR, GLC and mass spectral analyses contains the compounds having the structures:

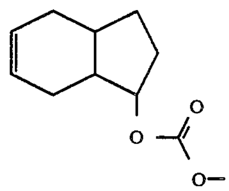
;
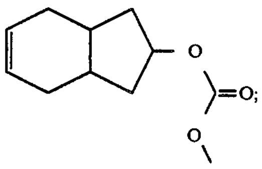
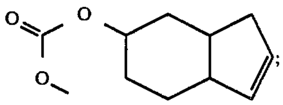
; and
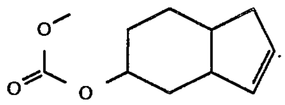

FIG. 9 is the GLC profile for the crude reaction product prior to distillation. The peak indicated by reference numeral 91 is the peak for the mixture of compounds having the structures:

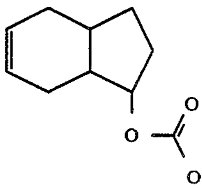
and
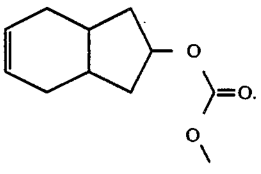

The peak indicated by reference numeral 92 is the peak for the mixture of compounds having the structures:

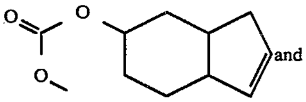
and
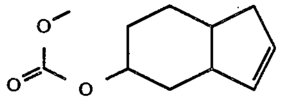

FIG. 10 is the GLC profile for bulked distillation Fractions 10–14 of the foregoing distillation (Conditions: 6'×0.25" 10% SE-30 column programmed at 220° C. isothermal). The single peak at 3.46 is the peak for the mixture of compounds having the structures:

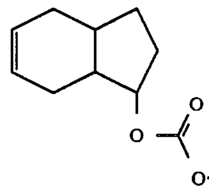
and
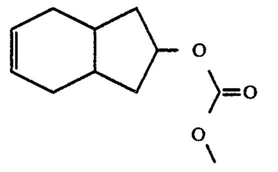

FIG. 11 is the NMR spectrum for peak 91 of the GLC profile of FIG. 9 for the compounds having the structures:

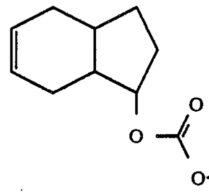
and
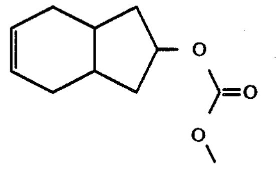

(Conditions: Field strength: 100 MHz; Solvent: $CFCl_3$).

FIG. 12 is the infra-red spectrum for peak 91 of the GLC profile of FIG. 9 for the compounds having the structures:

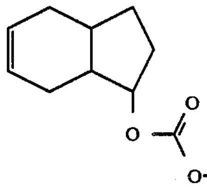
and
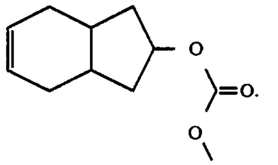

FIG. 13 is the NMR spectrum for peak 92 of the GLC profile of FIG. 9 for the compounds having the structures:

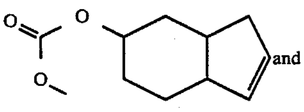
and
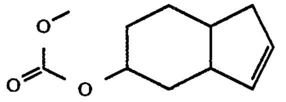

(Conditions: Field strength: 100 MHz; Solvent: $CFCl_3$).

FIG. 14 is the infra-red spectrum for the peak indicated by reference numeral 91 on the GLC profile of FIG. 9 for the compounds having the structures:

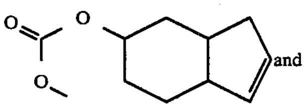
and
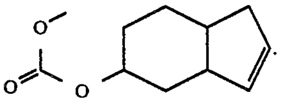

EXAMPLE III

Herbal Fragrance Formulation Prepared Using Product Prepared According to Example II

| Ingredients | Parts by Weight |
|---|---|
| Amyl cinnamic aldehyde | 20 |
| Phenyl acetaldehyde dimethyl acetal | 4 |
| Thyme oil white | 8 |
| Sauge scarlee French | 8 |
| Galbanum oil | 4 |
| Juniper berry oil | 10 |
| Methyl octin carbonate | 4 |
| Linalyl acetate | 2 |
| Dihydro methyl jasmonate | 10 |
| The bicyclononenyl carbonate mixture prepared according to Example II, bulked distillation Fractions 10–14 | 10 |

The composition of matter containing the bicyclononenyl methyl carbonate mixture prepared according to Example II adds a strong strawberry-like aroma with green, banana topnotes to this herbal fragrance formulation. Accordingly, the resulting formulation can be termed as "herbal with strawberry-like undertones and green banana topnotes.

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Mixture of bicyclononenyl methyl carbonates prepared according to Example II (bulked Fractions 10–14). | A strawberry-like aroma with green banana topnotes. |
| Fragrance formulation of Example III. | Herbal with strawberry-like undertones and green banana topnotes. |

EXAMPLE V

Perfumed Liquid Detergents

Concentrated liquid detergents (lysine salt of n-dodecylbenzene sulfonic acid as more specifically described in U.S. Pat. No. 3,948,818 issued Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of Colognes and Handkerchief Perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

Preparation Of Soap Compositions

One hundred grams of soap chips (per sample) (IVORY ® produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres, pressure at 180° C. for a period of three hours and the resulting liquids are placed into soap molds. The resulting soap cakes, on cooling, manifest aromas as set forth in Table I of Example IV.

EXAMPLE VIII

Preparation Of Solid Detergent Compositions

Detergents are prepared using the following ingredients according to Example I of Canadian Pat. No. 1,007,948 (incorporated by reference herein):

| Ingredient | Percent by Weight |
|---|---|
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), non-woven cloth substrates useful as drieradded fabric softening articles of manufacture are prepared wherein the substrate, the substrate coating, the outer coating and the perfuming material are as follows:

1. A water "dissolvable" paper ("Dissolvo Pater");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabic softener non-woven fabrics and these aroma characteristics are described in Table I of Example IV, supra,

EXAMPLE X

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid prepared by the Dow Corning Corporation | 0.10 weight percent |
| Tween 20 surfactant (prepared by ICI America Corporation) | 0.03 weight percent |
| One of the perfumery substances as set forth in Table I of Example IV | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stephanol WAT produced by the Stephan Chemical Company (35.0 weight percent). The resulting mixture is heated to 60° C. and mixed until a clear solution is obtained (at 60° C.). This material is "Composition A".

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example IV to the mixture. The resulting mixture is cooled to 40° C. and blending is carried out for an additional one hour in each case. At the end of this blending period, the resulting material has a pleasant fragrance as indicated in Table I of Example IV.

What is claimed is:

1. A product produced according to the process of reacting formic acid with bicyclononadiene to form a bicyclononenyl formate-containing mixture according to the reaction:

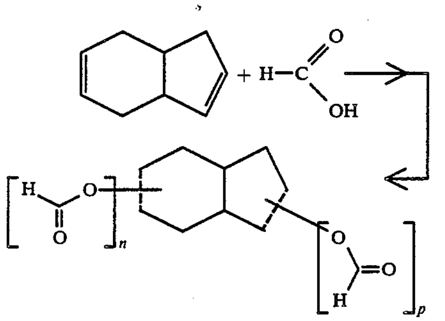

and then reacting the resulting bicyclononenyl formate-containing mixture with a dialkyl carbonate defined according to the structure:

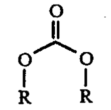

according to the reaction:

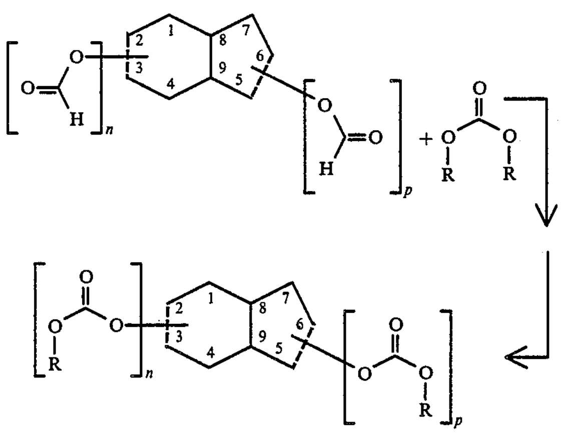

in the presence of an alkali metal alkoxide or aluminum isopropoxide catalyst at a temperature in the range of from 50° C. up to 90° C. wherein (a) in the compounds indicated by the structures having dashed lines such structures represent mixtures and in the mixtures in each of the compounds, one of the dashed lines represents a carbon-carbon double bond and the other of the dashed lines represents a carbon-carbon single bond; wherein N and P each represents 0 or 1; wherein R represents methyl or ethyl; with the provisos that when N is 0, P is 1 and when P is 0, N is 1; and when N is 1, the dashed line at the "2-3" position is a carbon-carbon single bond, the moieties:

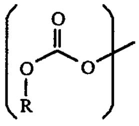 and 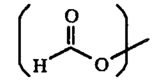

are bonded to the moiety:

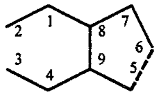

at the "2" or "3" position and the dashed line at the "5-6" position is a carbon-carbon double bond; and when P is 1, the dashed line at the "5-6" position is a carbon-carbon single bond, the moieties:

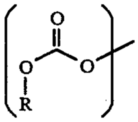 and 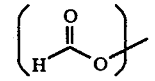

are bonded to the moiety:

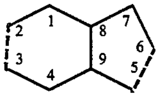

at the "5" or "6" position and the dashed line at the "2-3" position is a carbon-carbon double bond; (b) the mole ratio of formic acid:bicyclononadiene is from about 2:1 up to about 7:1; and (c) the mole ratio of dialkyl carbonate:bicyclononenyl formate is from about 2:1 up to about 4:1.

2. The product of claim 1 wherein R represents methyl.

3. A process for augmenting or enhancing the aroma of a consumable material selected from the group consisting of perfume compositions, colognes and perfumed articles comprising the step of adding to said consumable material an aroma augmenting or enhancing quantity of the product defined according to claim 1.

4. The process of claim 3 wherein the consumable material is a perfume composition or cologne.

5. The process of claim 3 wherein the consumable material is a perfumed article and the perfumed article is a solid or liquid anionic, cationic, nonionic or zwitterionic detergent.

6. The process of claim 2 wherein the consumable material is a perfumed article and the perfumed article is a fabric softener composition or fabric softener article.

7. The process of claim 2 wherein the consumable material is a perfumed article and the perfumed article is a perfumed polymer.

8. A process for augmenting or enhancing the aroma of a consumable material selected from the group consisting of perfume compositions, colognes and perfumed articles comprising the step of adding to said consumable material an aroma augmenting or enhancing quantity of the product defined according to claim 2.

9. The process of claim 8 wherein the consumable material is a perfume composition or cologne.

10. The process of claim 8 wherein the consumable material is a perfumed article and the perfumed article is a solid or liquid anionic, cationic, nonionic or zwitterionic detergent.

11. The process of claim 8 wherein the consumable material is a perfumed article and the perfumed article is a fabric softener composition or fabric softener article.

12. The process of claim 8 wherein the consumable material is a perfumed article and the perfumed article is a perfumed polymer.

13. The product produced according to the process of reacting formic acid with bicyclononadiene to form a bicyclononenyl formate-containing mixture according to the reaction:

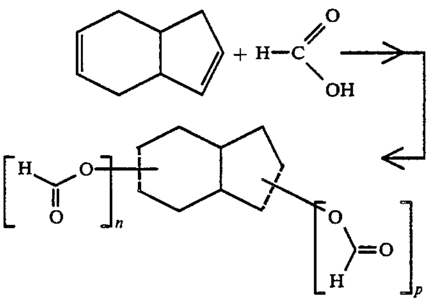

wherein (a) in the compounds indicated by structures having dashed lines, such structures represent mixtures and in the mixtures in each of the compounds one of the dashed lines represents a carbon-carbon double bond and the other of the dashed lines represents a carbon-carbon single bond; wherein N and P each represents 0 or 1; with the provisos that when N is 0, P is 1 and when P is 0, N is 1; and when N is 1, the dashed line at the "2-3" position is a carbon-carbon single bond, the moiety having the structure:

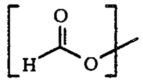

is bonded to the moiety having the structure:

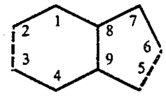

at the "2" or "3" position and the dashed line at the "5-6" position is a carbon-carbon double bond; and when P is 1, the dashed line at the "5-6" position is a carbon-carbon single bond, the moiety having the structure:

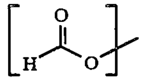

is bonded to the moiety having the structure:

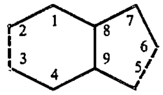

at the "5" or "6" position and the dashed line at the "2-3" is a carbon-carbon double bond, and (b) the mole ratio of formic acid:bicyclononadiene varies from about 2:1 up to about 7:1.

* * * * *